(12) United States Patent
Tang et al.

(10) Patent No.: US 7,321,129 B2
(45) Date of Patent: Jan. 22, 2008

(54) DEPOSITION SYSTEM AND FILM THICKNESS MONITORING DEVICE THEREOF

(75) Inventors: Shing-Dar Tang, Taoyuan Hsien (TW); Sean Chang, Taoyuan Hsien (TW)

(73) Assignee: Delta Electronics, Inc., Kuei San, Taoyuan Hsien (TW)

( * ) Notice: Subject to any disclaimer, the term of this patent is extended or adjusted under 35 U.S.C. 154(b) by 19 days.

(21) Appl. No.: 11/189,868

(22) Filed: Jul. 27, 2005

(65) Prior Publication Data

US 2006/0033057 A1 Feb. 16, 2006

(30) Foreign Application Priority Data

Jul. 30, 2004 (TW) .............................. 93122864 A

(51) Int. Cl.
*G01N 21/86* (2006.01)
(52) U.S. Cl. ............................................. 250/559.27
(58) Field of Classification Search ........... 250/559.27, 250/559.4
See application file for complete search history.

(56) References Cited

U.S. PATENT DOCUMENTS

| 3,871,771 | A | * | 3/1975 | Scott | 356/364 |
| 5,568,256 | A | * | 10/1996 | Korner et al. | 356/512 |
| 2001/0011712 | A1 | * | 8/2001 | Castenmiller et al. | 250/548 |
| 2003/0089690 | A1 | * | 5/2003 | Yamazaki et al. | 219/121.66 |
| 2003/0193672 | A1 | * | 10/2003 | Okada et al. | 356/630 |
| 2003/0197874 | A1 | * | 10/2003 | Moghaddam et al. | 356/630 |

* cited by examiner

*Primary Examiner*—Que Tan Le
*Assistant Examiner*—Kevin Wyatt
(74) *Attorney, Agent, or Firm*—Birch, Stewart, Kolasch & Birch, LLP

(57) ABSTRACT

A deposition system and film thickness monitoring device thereof. The film thickness monitoring device for monitoring thickness of a thin film coated on an optical substrate includes a laser light source, a retro-reflector, and a light receiver. The laser light source and the retro-reflector are disposed on opposite sides of the optical substrate. First, a light beam is emitted by the laser light source and then passes through the thin film along a first path. Second, the light beam is reflected by the retro-reflector and then passes through the thin film again along a second path parallel to the first path. Third, the light beam is received by the light receiver.

19 Claims, 3 Drawing Sheets

DEPOSITION SYSTEM AND FILM THICKNESS MONITORING DEVICE THEREOF

BACKGROUND

The invention relates to a deposition system, and in particular to a deposition system and film thickness monitoring device thereof.

Due to rapid development in optical industries in recent years, high performance of optical elements is required. Thus, optical deposition accuracy of the optical elements is strictly controlled such that a film thickness monitoring device is often utilized to monitor film thickness during optical deposition process.

Conventional film thickness monitoring devices can be categorized into reflection and transmission monitoring types. FIG. 1A shows a reflection monitoring device 100. When a laser light source 102 emits a light beam onto an optical thin film 106 on an optical substrate 104, a portion of the light is reflected and received by a light receiver 108, measuring thickness of the optical thin film. As shown in FIG. 1A, since the laser light source 102 and light receiver 108 are disposed on the same side of the optical substrate 104, a volume of the reflection monitoring device 100 is reduced and the reflection monitoring device 100 can be disposed on an exterior side of a vacuum chamber of a sputtering coater for film deposition for easy installation and repair. Since film thickness is measured from the reflected light, however, if the substrate is inclined, the reflected light may deviate from the receiving range of the light receiver 108, such that installation and angle calibration of the optical substrate 104 are sensitive. Particularly, design of the optical deposition machine can contain hundreds of optical substrates, such that it is difficult to measure each optical substrate thereof.

FIG. 1B shows a transmission monitoring device 200. The laser light source 202 and the light receiver 202 are disposed on two sides of the optical substrate 204, respectively, such that the light receiver 208 receives laser light beam passing through the optical thin film 206, to prevent light deviation due to inclination of the optical substrate. The arrangement of the laser light source 202 and the light receiver 202 on both sides of the optical substrate 204 increases the total volume of the machine and is difficult to install.

SUMMARY

Embodiments of the invention provide a film thickness monitoring device to eliminate the shortcomings of conventional reflection monitoring device and transmission monitoring device, thereby providing high accuracy.

Also provided is a film thickness monitoring device comprising a laser light source, a retro-reflector, and a light receiver. The laser light source and the retro-reflector are disposed on opposite sides of the optical substrate. First, a light beam is emitted by the laser light source and then passes through the thin film along a first path. Second, the light beam is reflected by the retro-reflector and then passes through the thin film again along a second path parallel to the first path. Third, the light beam is received by the light receiver.

Thus, the film thickness is measured from the light passing through the optical thin film, not by reflected light from the optical substrate. Thus, the problem of inaccurate installation of the optical substrate at an angle, deviating from receiving the range of the light receiver, is solved.

Moreover, since the laser light source and the light receiver are disposed on the same side, the total volume is reduced. The laser light source and the light receiver can be disposed on an exterior side of a vacuum chamber of a sputtering coater for film deposition such that installation and repair are convenient. Furthermore, the light beam received by the light receiver passes the optical thin film twice, such that sensitivity of the measured value of the light receiver is increased, thereby improving accuracy.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the subsequent detailed description and the accompanying drawings, which are given by way of illustration only, and thus are not limitative of the present invention, and wherein.

DETAILED DESCRIPTION

Figure 1A:
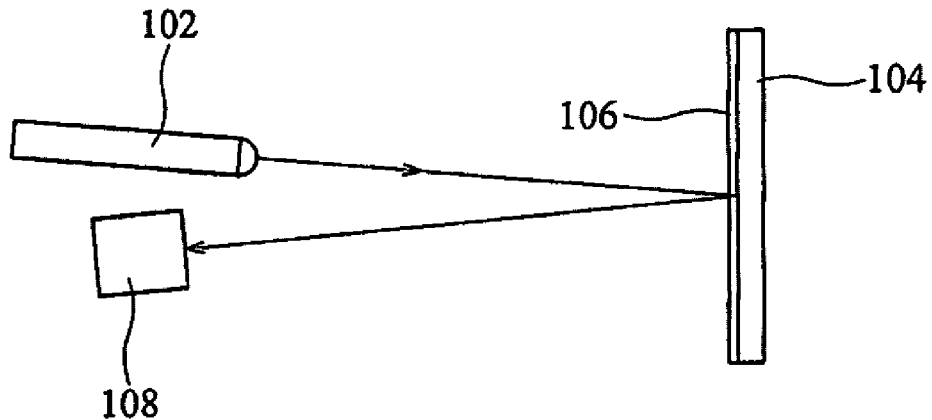
FIG. 1A is a schematic view of a conventional reflection film thickness monitoring device.
Figure 1B:
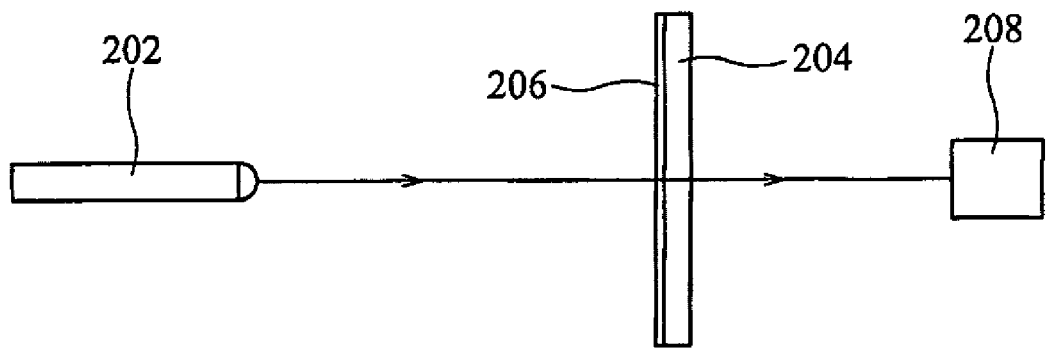
FIG. 1B is a schematic view of a conventional transmission film thickness monitoring device.
Figure 2:
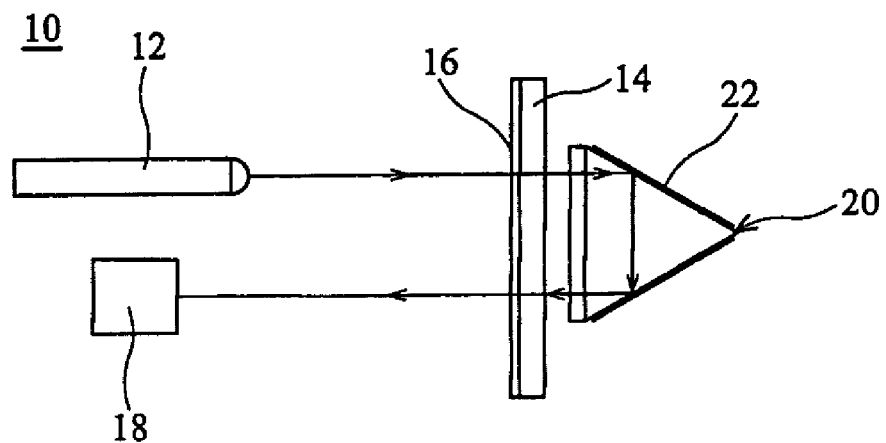
FIG. 2 is a schematic view of a film thickness monitoring device of an embodiment of the invention.

FIG. 2 is a schematic view of a film thickness monitoring device 10 of an embodiment of the invention. The film thickness monitoring device 10 comprises a laser light source 12, a light receiver 18, and a retro-reflector 20. The laser light source 12 and the light receiver 18 are disposed on the same side of the optical substrate 14, and the retro-reflector 20 is disposed on an opposite side thereof. The retro-reflector 20 can reflect a light along a light path parallel to that of the incident light from the laser light source 12, with none dispersed. In the embodiment, the retro-reflector 20 comprises a corner cube prism structure.

Additionally, the retro-reflector 20 can be polygonal prism, such as triangular, quadrangular, pentagonal, or hexagonal, or a polygonal reflector with double reflection faces, triple reflection faces, quadrilateral reflection faces, pentahedral reflection faces, hexahedral reflection faces, or a combination thereof.

After an light emitted by the laser light source 12 passes through the optical thin film 16 and the optical substrate 14, the light reaches the retro-reflector 20. The light reflected from retro-reflector 20 is along a path parallel to that of the incident light to pass through the optical thin film 16. The light receiver 18 is disposed along the light path of the light reflected from retro-reflector 20 after passing through the optical thin film 16 to receive the light. Thus, thickness of the optical thin film 16 can be accurately measured.

In the optical structure utilizing the retro-reflector 20, the light emitted by the laser light source 12 finally reaches the light receiver 18. The film thickness is measured by the light passing through the optical thin film 16, not by reflected light from the optical substrate 14. Thus, problems of optical substrate 14 inclination and deviation from receiving range of the light receiver 18 are solved. That is, since light is not reflected by the optical substrate 14, but passes through the optical substrate 14 and the optical thin film 16 in a parallel path, if the optical substrate 14 is slightly inclined, the incident angle of the light at the light receiver 18 is not changed. Moreover, since the laser light source 12 and the light receiver 18 are disposed on the same side, the total volume is reduced. The laser light source 12 and the light receiver 18 can be disposed on an exterior side of a vacuum chamber (not shown) of a sputtering coater for film deposition such that installation and repair are convenient. Thus, the invention eliminates disadvantages of the conventional reflection and transmission film thickness monitoring devices and preserves advantages of them.

In addition, a light emitted by the laser light source 12 passes through the optical thin film 16 once, and then the light reflected by the retro-reflector 20 passes through the optical thin film 16 again to reach the light receiver 18. That is, the light beam received by the light receiver 18 can pass the optical thin film 16 twice such that sensitivity of the measured value of the light receiver 18 is increased, and then the accuracy of film thickness can be increased.

As shown in FIG. 2 again, the retro-reflector 20 can be deposited with a total reflection deposition layer 22, ensuring that the reflected light can be totally reflected by the retro-reflector 20, reducing energy loss due to light refraction to the exterior. In addition, the retro-reflector 20 can be directly fixed on the optical substrate 14, facing a rear lateral surface of the laser light source, or disposed at a distance away from the optical substrate 14.

Figure 3:
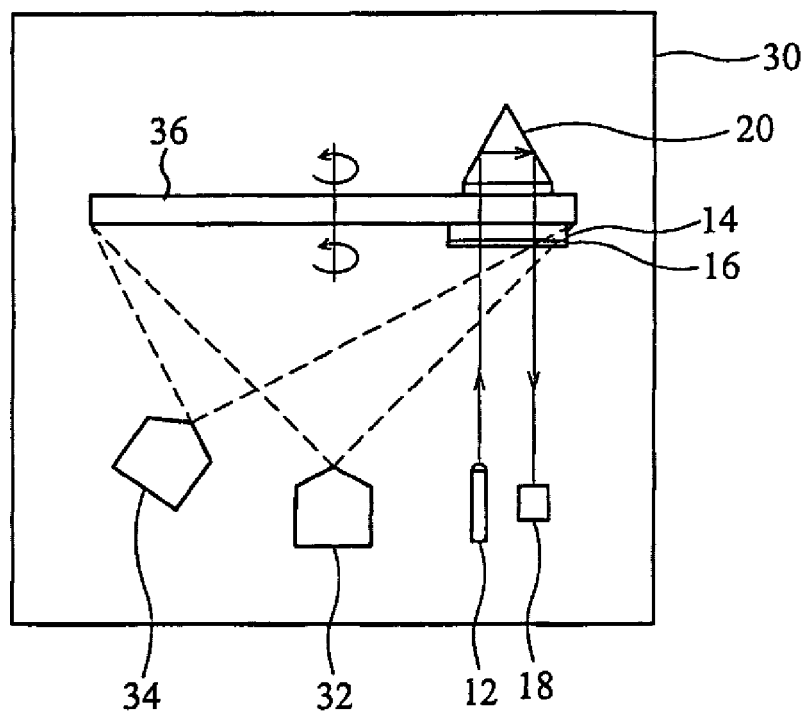
FIG. 3 is a schematic view of a film thickness monitoring device applied in ion-beam assisted deposition of an electron-beam gun evaporation source.

FIG. 3 is a schematic view of a film thickness monitoring device applied in an ion-beam assisted deposition (IAD) of an electron-beam gun evaporation.

As shown in FIG. 3, an electron-beam gun evaporation source 32 and an assisted deposition of an independent ion-beam source 34 are disposed in the vacuum chamber 30 of a sputtering coater for film deposition. The film material is evaporated into a gaseous phase by high speed electron impact. The ion-beam source 34 increases film piling density and purity. In the vacuum chamber 30, the optical substrate 14 is fixed on a clamped rotary plate 36 rotating at a constant rate. The clamped rotary plate 36 is a carrier. The film material evaporated into gas is deposited on the optical substrate 14 to form an optical thin film 16. The retro-reflector 20 is fixed on the clamped rotary plate 36, corresponding to the rear lateral side of the optical substrate 14. When the clamped rotary plate 36 rotates to a position, which is that the light beam emitted by the laser light source 12 can pass through the optical thin film 16, the retro-reflector disposed on the rear lateral side of the optical substrate 14 reflects the light beam passing through the optical thin film 16 along a path parallel to the incident light. The light passes through the optical thin film 16 again, and is received by the light receiver 18 at the same side as the laser light source 12.

Figure 4:
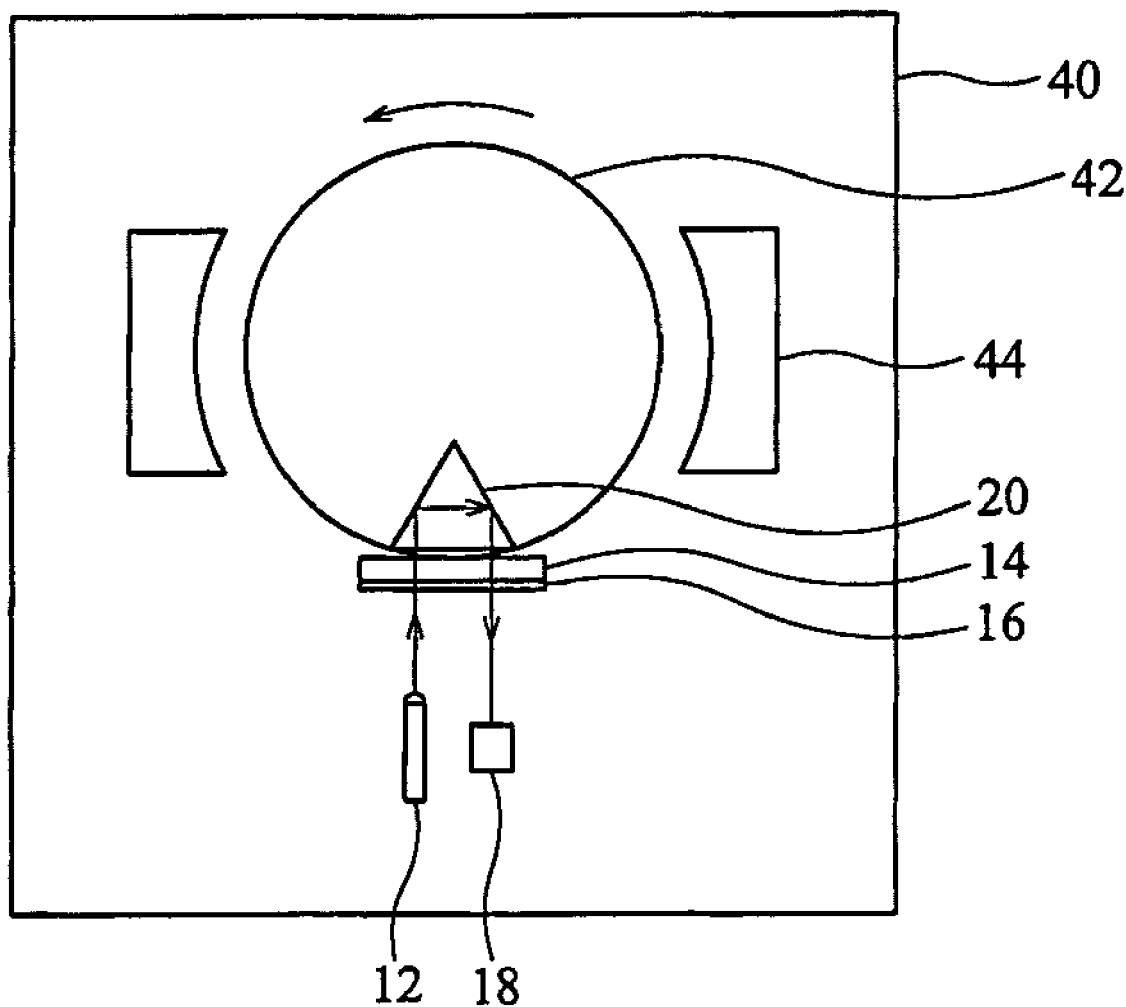
FIG. 4 is a schematic view of an embodiment of a film thickness monitoring device applied in plasma sputtering.

FIG. 4 is a schematic view of an embodiment of a film thickness monitoring device applied in plasma sputtering. As shown, in a vacuum chamber 40, the optical substrate 14 and the retro-reflector 20 correspond to each other, fixed at two sides of a clamped cylinder 42 rotating at a constant rate, respectively. The clamped cylinder 42 is a carrier. Reactive ion impact target 44 is dissociated by high pressure such that an optical thin film 16 is deposited on the optical substrate 14. When the clamped cylinder 42 rotates to a position, which is that the light beam emitted by the laser light source 12 can pass through the optical thin film 16, the light beam is reflected by the retro-reflector 20, passes through the optical thin film 16 again, and then is received by the light receiver 18 at the same side as the laser light source 12.

As described, the film thickness monitoring device of the invention can be applied in many methods of film deposition. The film thickness monitoring device can be adequately combined with any substrate clamping mechanism inside the film deposition chamber. The laser light source 12 and the light receiver 18 can be installed together on an exterior side of the film deposition chamber for easy installation and repair. In addition, the optical thin film 16 can be directly formed on the clamping mechanism.

Furthermore, although the retro-reflector 20 is fixed on the clamping mechanism as an example, the invention is not limited thereto. The retro-reflector 20 can be fixed on other tools, or disposed at a distance away from the clamping mechanism, in light path of the light beam emitted by the laser light source 12 for reflection. Additionally, the invention does not limit the number of laser light sources 12, light receivers 18, or retro-reflectors 20. Quantities of retro-reflector and light source can be the same or different, depending on the arrangement and quantities of the optical substrates 14 in the film deposition chamber.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A device for monitoring thickness of a thin film coated on an optical substrate, comprising:
    at least one light source emitting a light beam passing through the thin film along a first path;
    at least one retro-reflector for reflecting the light beam such that the light beam passes through the thin film along a second path parallel to the first path;
    at least one light receiver for receiving the light beam passing through the thin film along the second light path; and
    a clamping mechanism rotating at a constant speed for disposing the optical substrate thereon, wherein, when the thin film is rotated to be in the first path, the light beam of the light source passes through the thin film.

2. The device as claimed in claim 1, wherein the retro-reflector comprises at least one corner cube prism, polygonal prism, polygonal reflector, reflector deposited with a total reflection deposition layer, or a combination thereof.

3. The device as claimed in claim 1, wherein the quantities of the retro-reflector and the light source are different.

4. The device as claimed in claim 1, wherein the optical substrate is fixed on a surface of a clamping mechanism.

5. The device as claimed in claim 4, wherein the retro-reflector is disposed on a side of the clamping mechanism opposite to the light source.

6. The device as claimed in claim 4, wherein the retro-reflector is fixed on the surface of the clamping mechanism, or disposed at distance away from the clamping mechanism.

7. The device as claimed in claim 4, wherein the clamping mechanism comprises clamped rotary plates, clamped cylinders, or a combination thereof.

8. The device as claimed in claim 1, wherein the light source is a laser light source.

9. A deposition system, comprising:
- at least one film deposition source having electron-beam gun evaporation sources, ion sources, targets, or a combination thereof, for optical deposition;
- at least one carrier for supporting an optical substrate to deposit a thin film thereon;
- at least one light source emitting a light beam, passing through the thin film along a first path;
- at least one retro-reflector for reflecting the light beam to pass through the thin film along a second path parallel to the first path; and
- at least one light receiver receiving the light beam passing through the thin film along the second light path; and a clamping mechanism rotating at a constant speed for disposing the optical substrate thereon, wherein, when the thin film is rotated to be in the first path, the light beam of the light source passes through the thin film.

10. The deposition system as claimed in claim 9, further comprising a chamber, containing the film deposition source, the carrier, the light source, the retro-reflector, and a light receiver, or a combination thereof.

11. The deposition system as claimed in claim 9, wherein the retro-reflector comprises at least one corner cube prism, polygonal prism, polygonal reflector, reflector deposited with a total reflection deposition layer, or a combination thereof.

12. The deposition system as claimed in claim 9, wherein the retro-reflector is fixed on the surface of the carrier, or disposed at a distance away from the carrier.

13. The deposition system as claimed in claim 9, wherein the quantities of the retro-reflector and the light source are different.

14. The deposition system as claimed in claim 9, wherein the carrier comprises a clamping mechanism.

15. The deposition system as claimed in claim 9, wherein the carrier rotates at a constant speed, and when the thin film is rotated to be in the first path, the light beam of the light source passes through the thin film.

16. The deposition system as claimed in claim 9, wherein the retro-reflector is disposed on the optical deposition opposite to the light source.

17. The deposition system as claimed in claim 9, wherein the retro-reflector is fixed on the surface of the optical substrate, or disposed at a distance away from the optical substrate.

18. The deposition system as claimed in claim 9, wherein the light source is a laser light source.

19. A device for monitoring thickness of a thin film coated on an optical substrate comprising:
- at least one light source emitting a light beam passing through the thin film along a first path;
- at least one retro-reflector for reflecting the light beam such that the light beam passes through the thin film along a second path parallel to the first path; and
- at least one light receiver for receiving the light beam passing through the thin film along the second light path;
- wherein the optical substrate is fixed on a surface of a clamping mechanism and the clamping mechanism comprises clamped rotary plates, clamped cylinders, or a combination thereof.

* * * * *